(12) United States Patent
Shoichet et al.

(10) Patent No.: US 12,419,878 B2
(45) Date of Patent: Sep. 23, 2025

(54) SUSTAINED RELEASE LOCAL ANESTHETIC HYDROGEL COMPOSITION

(71) Applicant: THE GOVERNING COUNCIL OF THE UNIVERSITY OF TORONTO, Toronto (CA)

(72) Inventors: Molly Shoichet, York (CA); Michael J. Cooke, Toronto (CA); Sonja Ing, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 931 days.

(21) Appl. No.: 17/595,470

(22) PCT Filed: May 18, 2020

(86) PCT No.: PCT/CA2020/050666
§ 371 (c)(1),
(2) Date: Nov. 17, 2021

(87) PCT Pub. No.: WO2020/232539
PCT Pub. Date: Nov. 26, 2020

(65) Prior Publication Data
US 2022/0202793 A1 Jun. 30, 2022

Related U.S. Application Data

(60) Provisional application No. 62/849,671, filed on May 17, 2019.

(51) Int. Cl.
*A61K 31/445* (2006.01)
*A61K 9/00* (2006.01)
(Continued)

(52) U.S. Cl.
CPC .......... *A61K 31/445* (2013.01); *A61K 9/0024* (2013.01); *A61K 9/06* (2013.01);
(Continued)

(58) Field of Classification Search
None
See application file for complete search history.

(56) References Cited

U.S. PATENT DOCUMENTS 5,972,326 A  10/1999  Galin et al.
6,350,781 B1  2/2002  Shahinia, Jr.
(Continued)

FOREIGN PATENT DOCUMENTS

CA  2700262 A1  10/2009
CA  2700736 A1  10/2009
(Continued)

OTHER PUBLICATIONS

Fisher Scientific, Products, Methyl cellulose, viscosity 400 cp (2% solution in water) (Accessed Feb. 2025) (Year: 2025).*
(Continued)

*Primary Examiner* — Jeffrey S Lundgren
*Assistant Examiner* — Anthony Joseph Seitz
(74) *Attorney, Agent, or Firm* — Norton Rose Fulbright US LLP

(57) ABSTRACT

A bioresorbable, sustained release pharmaceutical composition comprising: 1.8 wt % to 3.0 wt % methylcellulose and 0.1 wt % to 3.0 wt % hyaluronan in the form of a gel polymer matrix, and at least one local anesthetic agent, suitably ropivacaine, which may be administered by injection.

28 Claims, 11 Drawing Sheets

(51) Int. Cl.
  *A61K 9/06* (2006.01)
  *A61K 31/167* (2006.01)
  *A61K 47/36* (2006.01)
  *A61K 47/38* (2006.01)
  *A61P 23/02* (2006.01)

(52) U.S. Cl.
  CPC ............ *A61K 31/167* (2013.01); *A61K 47/36* (2013.01); *A61K 47/38* (2013.01); *A61P 23/02* (2018.01)

(56) References Cited

U.S. PATENT DOCUMENTS

| | | |
|---|---|---|
| 6,764,678 B2 | 7/2004 | Weber et al. |
| 7,884,087 B1 | 2/2011 | Bellini et al. |
| 7,964,644 B2 | 6/2011 | Meyer |
| 8,455,465 B2 | 6/2013 | Gavard Molliard |
| 8,940,311 B2 | 1/2015 | Lim et al. |
| 8,980,248 B2 | 3/2015 | Shoichet et al. |
| 9,056,126 B2 | 6/2015 | Hersel et al. |
| 9,205,047 B2 | 12/2015 | Shoichet et al. |
| 9,782,490 B2 | 10/2017 | Tuzin |
| 9,814,675 B2 | 11/2017 | Oshry et al. |
| 2015/0018303 A1 | 1/2015 | Balazs et al. |
| 2016/0228613 A1 | 8/2016 | Gavard Molliard |
| 2016/0331865 A1 | 11/2016 | Vitally et al. |
| 2016/0346433 A1 | 12/2016 | Bon Betemps et al. |
| 2017/0151367 A1 | 6/2017 | Yu et al. |
| 2017/0333596 A1 | 11/2017 | Hagedorn et al. |
| 2018/0008586 A1 | 1/2018 | Iwakiri et al. |

FOREIGN PATENT DOCUMENTS

| | | | |
|---|---|---|---|
| CA | 2944734 A1 | 2/2010 | |
| CA | 2703807 | 11/2011 | |
| CA | 3078555 A1 | 4/2019 | |
| WO | WO-2010015901 A1 * | 2/2010 | .............. A61P 29/00 |
| WO | WO 2015/015407 | 2/2015 | |
| WO | WO 2015/097261 | 7/2015 | |
| WO | WO 2017/069672 | 4/2017 | |

OTHER PUBLICATIONS

Ngai, Local Delivery System to Reduce Pain in a Model of Back Surgery, Master's Thesis, University of Toronto, 2016 (Year: 2016).*

Ko et al., The Spine Journal, vol. 19, Issue 4, 2019, pp. 578-586 (Year: 2019).*

Extended European Search Report issued in European Patent Application No. 20810650.0, dated Apr. 11, 2023.

Gupta et al., "Fast-gelling injectable blend of hyaluronan and methylcellulose for intrathecal, localized delivery to the injured spinal cord," Biomaterials, 27(11):2370-2379, 2006.

International Search Report and Written Opinion for Application No. PCT/CA2020/050666, mailed Aug. 3, 2020, 11 pages.

Kang C. et al.: A New Paradigm for Local and Sustained Release of Therapeutic Molecules to the Injured Spinal Cord for Neuroprotection and Tissue Repair. Tissue Engineering Part A 2009, vol. 15, No. 3, 595-604.

Lirk P. et al.: Local anaesthetics, European Journal of Anaesthesiology: Nov. 2014, vol. 31, Issue 11, p. 575-585. doi: 10.1097/EJA.0000000000000137.

Mulroy, M.F., Systemic toxicity and cardiotoxicity from local anesthetics: incidence and preventive measures. Reg. Anesth. Pain Med. 2002. 27(6): p. 556-61.

Pitcher G.M. et al.: Paw withdrawal threshold in the von Frey hair test is influenced by the surface on which the rat stands. J Neurosci Methods, 15 1999. 87(2): p. 185-93.

Sakura S et al., The comparative neurotoxicity of intrathecal lidocaine and bupivacaine in rats. Anesthesia & Analgesia, 2005. 101(2): p. 541-7.

Shamji M.F et al.: "Gait abnormalities and inflammatory cytokines in an autologous nucleus pulposus model of radiculopathy." Spine vol. 34,7 (2009): 648-54. doi:10.1097/BRS.0b013e318197f013.

Sun, Y.G. and Chen, Z. F.: *A gastrin-releasing peptide receptor mediates the itch sensation in the spinal cord.* Nature, 2007. 448(7154): p. 700-3.

Takenami T., et al., Neurotoxicity of intrathecally administered bupivacaine involves the posterior roots/posterior white matter and is milder than lidocaine in rats. *Regional Anesthesia and Pain Medicine,* 2005. 30(5): p. 464-472.

Wang Y. et al.: *Hydrogel delivery of erythropoietin to the brain for endogenous stem cell stimulation after stroke injury.* Biomaterials, 2012. 33(9): p. 2681-92.

Werdehausen R. et al.: Apoptosis induction by different local anaesthetics in a neuroblastoma cell line, *BJA: British Journal of Anaesthesia,* vol. 103, Issue 5, Nov. 2009, pp. 711-718, https://doi.org/10.1093/bja/aep236.

* cited by examiner

SUSTAINED RELEASE LOCAL ANESTHETIC HYDROGEL COMPOSITION

This application is a national phase application under 35 U.S.C. § 371 of International Application No. PCT/CA2020/050666 filed May 18, 2020, which claims priority from United States Application No. 62/849,671 filed May 17, 2019 which are incorporated herein by reference.

TECHNICAL FIELD

This invention relates to local anesthetic pharmaceutical compositions and methods of administering local anesthetic compounds.

BACKGROUND OF THE ART

Post-surgical pain is challenging to manage, often requiring opioids. Prolonged release of local anesthetics (i.e., lidocaine, bupivacaine, ropivacaine) provides an alternative to the use of opioids; however, there is currently no effective long-acting local anesthetic.

BRIEF SUMMARY

In one embodiment, there is provided a pharmaceutical composition comprising: 1.8 wt % to 3 wt % methylcellulose and 0.1 wt % to 3 wt % hyaluronan in the form of a gel polymer matrix, and at least one local anesthetic agent.

In one embodiment, the methylcellulose has a molecular weight between 2,000 g/mol and 500,000 g/mol and the hyaluronan has a molecular weight between 100,000 g/mol and 3,000,000 g/mol.

In one embodiment, the pharmaceutical composition includes between 1.8 wt % and 2.2 wt % methylcellulose and between 1.0 wt % and 2.0 wt % hyaluronan.

The pharmaceutical composition may be injected.

The local anesthetic agent may be an amide local anesthetic, which may be lidocaine, bupivacaine, ropivacaine, or a pharmaceutically acceptable salt thereof. The local anesthetic agent may be hydrophobic.

The methylcellulose may have a viscosity at or above 400 cP.

In some embodiments, less than 90%, less than 80%, less than 70%, less than 60%, less than 50%, less than 40%, less than 30%, less than 20%, less than 10% or less than 5% of the local anesthetic agent is released from the pharmaceutical composition within 24 hours of administration, within 48 hours of administration or within 72 hours of administration.

In some embodiments 20% or less, 30% or less, 40% or less, 50% or less, 60% or less, 70% or less, 80% or less, 90% or less, or 95% or less of the pharmaceutical composition remains at the site of administration after 1 day, after 2 days, after 3 days or after 7 days.

In one embodiment, the local anesthetic agent has both an acidic and basic form and the Cmax of the local anesthetic in the pharmaceutical composition is no greater than the Cmax of a corresponding dose of the local anesthetic in solution form when administered locally via injection.

In one embodiment, the local anesthetic agent has both an acidic form and a basic form and the percentage of the local anesthetic agent in the acidic form and basic form is between 0 to 40% acidic form and 60% to 100% basic form, in one embodiment between 0.1% to 27% acidic form and 73% to 99.9% basic form, based on the total weight of the local anesthetic.

In one embodiment, the pharmaceutical composition consists or consists essentially of: 0.4 to 2.4 wt % hyaluronan; 1.8 to 3.0 wt % methylcellulose; 0.5 to 1.5 wt % of an acid addition salt of the local anesthetic; and 10 to 40 wt % of free-base particles of the local anesthetic; with the remainder of the composition being water and biocompatible buffers and/or salts.

Also provided is a dosage form of between 1 mL and 100 mL of a pharmaceutical composition as described herein. The dosage form may include between 100 mg and 2000 mg (more specifically between 350 mg and 2000 mg or between 750 mg and 1500 mg) of the local anesthetic agent.

Also provided is a drug depot including (i) an aqueous carrier, (ii) from 0.50 to 1.50 wt % (e.g., 0.8±0.2, 1.0±0.2, or 1.2±0.2 wt %) of an acid addition salt of an anesthetic selected from lidocaine, bupivacaine, and ropivacaine dissolved in the aqueous carrier, and (iii) from 10 to 50 wt % (e.g., 15±5, 25±5, or 35±5 wt %) of free-base particles of an anesthetic selected from lidocaine, bupivacaine, and ropivacaine suspended in the aqueous carrier. In some embodiments, the aqueous carrier is a biocompatible aqueous gel. In particular embodiments, following administration to a subject, the drug depot provides localized anesthetic effects for a period of greater than 48 hours, greater than 72 hours, or greater than 96 hours.

In certain embodiments, the drug depot includes pharmaceutical compositions as described herein. In some embodiments, the drug depot includes (i) a biocompatible aqueous gel including between 1.8 wt % and 2.2 wt % methylcellulose and between 1.0 wt % and 2.0 wt % hyaluronan, (ii) from 0.80 to 1.20 wt % of an acid addition salt of ropivacaine dissolved in the biocompatible aqueous gel, and (iii) from 14 to 18 wt % of ropivacaine free-base particles suspended in the biocompatible aqueous gel. In other embodiments, the drug depot includes (i) a biocompatible aqueous gel including between 1.8 wt % and 2.2 wt % methylcellulose and between 1.0 wt % and 2.0 wt % hyaluronan, (ii) from 0.80 to 1.20 wt % of an acid addition salt of ropivacaine dissolved in the biocompatible aqueous gel, and (iii) from 30 to 36 wt % of ropivacaine free-base particles suspended in the biocompatible aqueous gel.

The remainder of the drug depot may be made up of water and biocompatible buffer(s) and/or salt(s).

The free-base particles may have a size distribution in which the median diameter D(50) is between 5 μm and 100 μm (e.g., 10±5, 20±10, or 80±20 μm).

Also provided is a pharmaceutical composition that includes a biocompatible gel and an active ingredient present in a first form, which is more soluble in the biocompatible gel, and a second form, which is less soluble in the biocompatible gel, wherein in physiological conditions the first form is released from the biocompatible gel more quickly than the second form, which has a more extended release. In one embodiment, the biocompatible gel comprises methylcellulose and hyaluronan in the form of a gel polymer matrix. In one embodiment, the first form is an acidic form of the active ingredient and the second form is a basic form of the active ingredient and the pharmaceutical composition comprises between 0.1% and 40% acidic form and between 60% and 99.9% basic form based on the total of the active ingredient. The composition may be injectable and the active ingredient may be a local anesthetic.

Also provided are methods of treating or preventing pain by administering a therapeutically effective amount of a pharmaceutical composition, dosage form or drug depot as provided herein to a subject in need thereof.

In one embodiment, the pain is associated with a minimally invasive procedure and the therapeutically effective amount of the pharmaceutical composition, dosage form or drug depot is less than or equal to 20 mL. In one embodiment, less than 10 mL.

The pharmaceutical composition, dosage form or drug depot may be administered for surgical anesthesia, for the treatment of post-surgical pain, as a nerve block or for the treatment of post-burn pain. The subject may be undergoing a bunionectomy, orthopedic surgery or a hernia procedure.

Administration may be to a surgical site or the site of an incision.

Without limiting the foregoing, the subject may be in labor, may be undergoing a biopsy, or may be donating or receiving a skin graft.

Also provided are sterilized syringes prefilled with a pharmaceutical composition, a dosage form or a drug depot as described herein.

DETAILED DESCRIPTION

Figure 1:
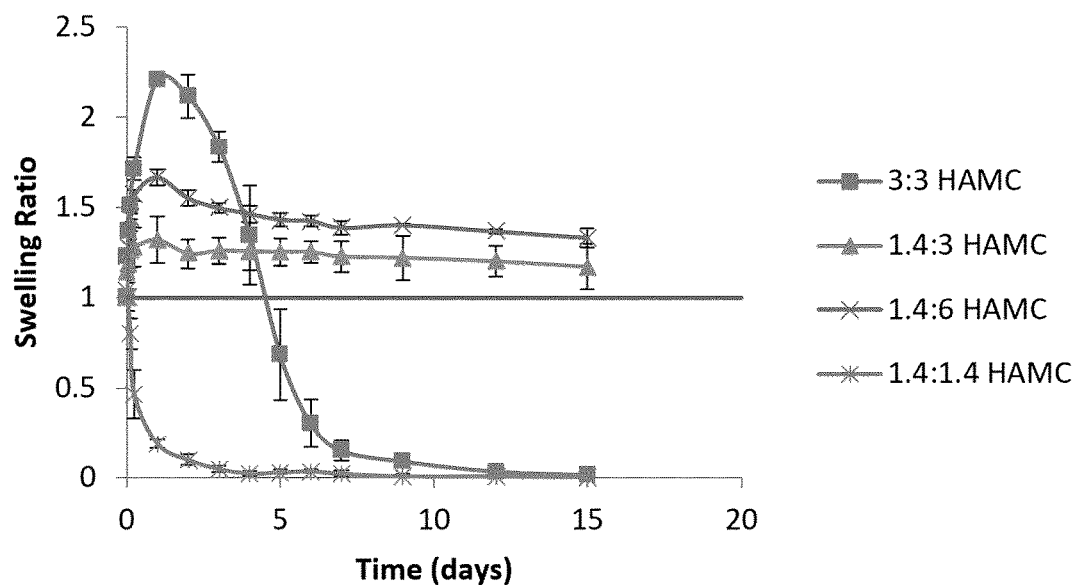
FIG. 1 is a graph showing the minimal swelling of certain compositions of HAMC. The solid line indicates a swelling ratio of 1. The 1.4:3 HAMC evidenced minimal swelling.

Management of post-operative pain remains suboptimal as current treatment strategies do not sufficiently address patient needs. The current standard of care is to inject local anesthetics either directly into the incision or around a nerve to provide either local analgesia or a regional nerve block. Commonly administered analgesics include local anesthetics, which are voltage-gated sodium channel blockers and serve to block action potentials, preventing neuronal transmission of the painful stimulus. However, local anesthetics are typically delivered as a liquid bolus injection, leading to fast clearance from the injection site and rapid dispersion throughout the body.

Fast clearance from the site of administration results in short-lived pain relief, necessitating continuous infusion and/or the subsequent use of systemic analgesics, such as opioids, to adequately alleviate pain. Continuous delivery systems, such as pumps, have a long length of duration but require the insertion of a catheter, which is invasive and carries the risk of infection. Systemic opioids are effective at providing pain relief, but are plagued by many adverse side effects, including addiction, respiratory depression, hyperalgesia, and nausea, constipation and vomiting.

Kang et al. previously investigated the resorption of a 2% HA to 7% MC gel in vivo (Kang et al. *A New Paradigm for Local and Sustained Release of Therapeutic Molecules to the Injured Spinal Cord for Neuroprotection and Tissue Repair*, TISSUE ENGINEERING: Part A Volume 14, No. 3, 2009). Briefly, HA was conjugated to a BODIPY-Fluorescent (BODIPY-FL) hydrazide and MC was conjugated to Texas Red hydrazide for visualization within the intrathecal (IT) space in rats. HA was found to degrade quickly, exhibiting a ~95% loss in fluorescent area after 24 h. In contrast, MC showed an initial degradation of ~65% after 24 h and then continued to persist within the IT space for at least 4 days. After 7 days, traces of neither HA nor MC could be detected. In view of this result, the ability of hydrogels having certain concentrations of HAMC as identified in the examples to increases the length of sensory block over a number of days in vivo was both surprising and unexpected.

In one embodiment, there is provided a sustained release pharmaceutical composition comprising a hydrogel and a local anesthetic. In a preferred embodiment, the local anesthetic is ropivacaine. In one embodiment, a dosage form comprises the local anesthetic in a basic form and in a salt form, and in a preferred embodiment the dosage form comprises a mixture of ropivacaine in the basic form and a pharmaceutically acceptable salt of ropivacaine, for example ropivacaine hydrochloride. In one embodiment, the composition is injectable.

In one embodiment, "sustained release" refers to a pharmaceutical composition that releases a local anesthetic such that the $C_{max}$ of the local anesthetic in the pharmaceutical composition is no greater than the $C_{max}$ of a corresponding dose of the local anesthetic in solution form when administered locally via injection.

In one embodiment, a single administered dose of a sustained release pharmaceutical composition as described herein provides localized anesthetic effects for a period of at least 12 hours; in other embodiments, at least 24 hours, at least 48 hours, at least 72 hours, for between 12 hours and 7 days, or for between 24 hours and 5 days.

In one aspect, there is provided a pharmaceutical composition comprising: 0.1 wt % to 3 wt % hyaluronan (HA) and 1.0 wt % to 3 wt %, preferably 1.8 wt % to 3 wt % methylcellulose (MC) in the form of a gel polymer matrix, and at least one local anesthetic agent. In one embodiment, the pharmaceutical composition comprises 1.0 to 2.0 wt % HA and 1.8 to 2.2 wt % MC. One embodiment comprises 1.3 to 1.5 wt % HA and 1.8 to 2.2 wt % MC, which composition is a bioresorbable sustained release composition that may be injected and is substantially eliminated from the site of administration within 28 days.

In one embodiment, the pharmaceutical composition comprises about 1.4 wt % HA and about 2.0 wt % MC.

As used herein, "biocompatible" means substantially free from deleterious effects on living systems or tissues. In surgery contexts, "biocompatible" means substantially free from inducing a serious rejection reaction.

In various embodiments, less than 90%, less than 80%, less than 70%, less than 60%, less than 50%, less than 40%, less than 30%, less than 20%, less than 10% or less than 5% of the local anesthetic agent is released from the pharmaceutical composition within 24 hours of administration. In various embodiments, less than 90%, less than 80%, less than 70%, less than 60%, less than 50%, less than 40%, less than 30%, less than 20%, less than 10% or less than 5% of the local anesthetic agent is released from the pharmaceutical composition within 48 hours of administration. In various embodiments, less than 90%, less than 80%, less than 70%, less than 60%, less than 50%, less than 40%, less than 30%, less than 20%, less than 10% or less than 5% of the local anesthetic agent is released from the pharmaceutical composition within 72 hours of administration.

Hyaluronic acid (or hyaluronan) (HA) is a linear polysaccharide composed of repeating disaccharide units of N-acetyl-glucosamine and D-glucuronic acid. HA is degraded enzymatically by hyaluronidase, which can be produced by cells. Its polymeric chains, of lengths of 10-15 thousand disaccharides, form random coils with large spheroidal hydrated volumes of up to 400-500 nm in diameter. Reactions can occur at the carboxyl group or the hydroxyl group of HA and also at the amino group when the N-acetyl group is removed.

Pharmaceutical grade HA is available in a wide variety of molecular weights, in the range of between about 100,000 and about 3,000,000 g/mol. In one embodiment the composition comprises HA in the range of 500,000 and 2,500,000 g/mol, in one embodiment in the range of 1,000,000 and 2,000,000 g/mol, and in a preferred embodiment in the range of 1,400,000 to 1,600,000 g/mol.

Blends of unmodified HA with a gelling polymer are injectable upon an application of force to a syringe because the shear-thinning properties of HA cause the polymer chains to straighten and align themselves, permitting flow through the needle. HA then returns to its high viscosity, zero shear structure upon exiting the needle as the polymeric chains once again become entangled amongst themselves.

The other polymer component of the hydrogel is methylcellulose (MC). MC is an example of a temperature sensitive gel, or a thermally reversible gel, that gels upon an increase in temperature. When the degree of substitution of hydroxyl groups with methyl groups is between 1.4 and 1.9 per monomer unit, MC has inverse thermal gelling properties. As the temperature increases, the methyl groups of MC form hydrophobic interactions and water molecules are released from interacting with MC, thereby forming a gel.

The MC may have a molecular weight in the range of between about 2,000 and about 1,000,000 g/mol. In one embodiment the composition comprises MC in the range of 10,000 and 500,000 g/mol, in one embodiment in the range of 100,000 to 400,000 g/mol, and in one embodiment in the range of 200,000 to 300,000 g/mol.

As used herein, "bioresorbable compositions" are compositions that can be dispersed by biological processes so that the composition or a percentage thereof cannot be detected at the site of administration.

In various embodiments, bioresorbable composition refers to a composition wherein >50%, >60%, >70%, >80%, >90% or >99% of the composition cannot be detected at the site of administration at 28 days post-administration. In one embodiment, the composition cannot be detected at the site of administration at 28 days post-administration.

In various embodiments, bioresorbable composition refers to a composition wherein >50%, >60%, >70%, >80%, >90% or >99% of the composition cannot be detected at the site of administration at 14 days post-administration. In one embodiment, the composition cannot be detected at the site of administration at 14 days post-administration.

In various embodiments, bioresorbable composition refers to a composition wherein >50%, >60%, >70%, >80%, >90% or >99% of the composition cannot be detected at the site of administration at 7 days post-administration. In one embodiment, the composition cannot be detected at the site of administration at 7 days post-administration.

In various embodiments, bioresorbable composition refers to a composition wherein >50%, >60%, >70%, >80%, >90% or >99% of the composition cannot be detected at the site of administration at 3 days post-administration. In one embodiment, the composition cannot be detected at the site of administration at 3 days post-administration.

In various embodiments, bioresorbable composition refers to a composition wherein >50%, >60%, >70%, >80%, >90% or >99% of the composition cannot be detected at the site of administration at 1 day post-administration. In one embodiment, the composition cannot be detected at the site of administration at 1 day post-administration.

The amount of composition at the site of administration may be detected by mass as would be determined by a person skilled in the art.

In one embodiment, the local anesthetic is an amide local anesthetic, examples of which include articaine, bupivacaine, cinchocaine dibucaine, etidocaine, levobupivacaine, lidocaine, mepivacaine, oxetacaine, prilocaine, ropivacaine, sameridine, tolycaine, tonicaine and trimecaine and pharmaceutically acceptable salts thereof, i.e. salts that retain the anesthetic activity of these compounds and do not impart undesired toxicological effects.

In one embodiment, the local anesthetic is lidocaine, bupivacaine, ropivacaine, and/or a pharmaceutically acceptable salt of any of the foregoing.

The composition may include two or more local anesthetics.

Specific formulations are 1.3:1.8 to 1.5:2.2 HA:MC (1.3 to 1.5 wt % HA, 1.8 to 2.2 wt % MC) for delivery of ropivacaine providing an injectable, bioresorbable, sustained release composition. In one embodiment, the pharmaceutical composition is substantially eliminated from the site of administration within 32 days, and in 7 days in a preferred embodiment.

Of the local anesthetics, bupivacaine and ropivacaine are of particular interest due to their potency and widespread clinical use. Both are similar structurally and functionally, differing only by a single methyl group; however, bupivacaine is a racemic mixture of R- and S-enantiomers, whereas ropivacaine is the enantiomerically pure S-enantiomer. Functionally, bupivacaine is more potent and ropivacaine is typically administered at higher doses. However, even at equipotent concentrations, bupivacaine is also more toxic than ropivacaine. As ropivacaine is less lipophilic than bupivacaine, it is less likely to penetrate large myelinated motor fibres, and it consequently has a more selective action on the pain-transmitting Aδ or C nerve fibres, rather than the Aβ fibres that are involved in motor function.

Ropivacaine is a promising and effective analgesic and would be of even greater value if its efficacy could be extended through sustained release. Various strategies to prolong the efficacy of ropivacaine have been investigated, including encapsulation of the drug within liposomes, microparticles or nanoparticles. While these strategies extend release and offer advantages over a liquid bolus injection, the particles do not remain localized and thus can be transported away from the surgery site, resulting in systemic side effects.

High doses of bupivacaine remain a concern clinically as they have been associated with dose-dependent cardiotoxicity, neurotoxicity and myotoxicity [Lirk, P., Picardi, S., and Hollmann, M. W., *Local anaesthetics: 10 essentials*. Eur J Anaesthesiol, 2014. 31(11): p. 575-85; Werdehausen, R., et al., *Apoptosis induction by different local anaesthetics in a neuroblastoma cell line*. British journal of anaesthesia, 2009. 103(5): p. 711-718; Mulroy, M. F., *Systemic toxicity and cardiotoxicity from local anesthetics: incidence and preventive measures*. Reg. Anesth. Pain Med. 2002. 27(6): p. 556-61; Takenami, T., et al., *Neurotoxicity of intrathecally administered bupivacaine involves the posterior roots/posterior white matter and is milder than lidocaine in rats*. Regional anesthesia and pain medicine, 2005. 30(5): p. 464-472.; Sakura, S., et al., *The comparative neurotoxicity of intrathecal lidocaine and bupivacaine in rats*. Anesthesia & Analgesia, 2005. 101(2): p. 541-7]. By comparison, ropivacaine has been found to reduce cardiovascular and neurologic complications at equipotent concentrations. The improved safety profile of ropivacaine has been attributed to its stereoselectivity and reduced lipophilicity relative to bupivacaine. Moreover, ropivacaine is metabolized by both cytochrome P50 (CYP) 1A2 and CYP3A4, while bupivacaine is metabolized mainly by CYP3A4. This further improves the safety profile for ropivacaine as the CYP3A4 bupivacaine receptor is common to many other drugs that patients may have been prescribed. Co-administration of these drugs with ropivacaine and bupivacaine may result in adverse pharmacokinetic interactions due to competition for CYP3A4; however, as ropivacaine is also largely metabolized by CYP1A2, adverse consequences are less likely to occur.

In one embodiment, the local anesthetic agent has both an acidic and basic form and the pharmaceutical composition comprises both the acidic and basic forms. For certain applications, an ideal release profile will have a rapid release so that the time of onset is short and a sustained release to provide the required duration of efficacy. In the case of treating post-surgical pain, this is needed so that the patient does not experience pain. Acidic and basic forms of a drug can have different solubilities. In the case of ropivacaine, the acidic form of ropivacaine is more soluble than the basic form and formulations having a greater percentage of the acidic form will have a greater initial release. In one embodiment, the ratio of the acidic form to the basic form is such that the $C_{max}$ of the local anesthetic in the pharmaceutical composition is no greater than the $C_{max}$ of a corresponding dose of the local anesthetic in solution form when administered locally (less than 40% of the acidic form in some embodiments and 13% of the acidic form in a preferred embodiment).

In one embodiment, the percentage of local anesthetic agent in the acidic form and basic form is between 0% and 40% acidic form and 60 and 100% basic form based on the total weight of the local anesthetic, in one embodiment between 0.1% and 27% acidic form and 73% and 99.9% basic form, and in a preferred embodiment between 2% and 20% acidic form and 80% and 98% basic form. In one embodiment, the pharmaceutical composition provides a burst release of local anesthetic followed by sustained release.

In one embodiment, the percentage of local anesthetic agent in the acidic form is less than 2% and basic form is greater than 98% and provides little or no burst release.

Pharmaceutical compositions as described herein may suitably be prepared through the physical blending of HA and MC in saline. After MC and HA are dispersed in saline and allowed to dissolve, the local anesthetic, suitably in particle form, may be dispersed in HAMC. The compositions may be sterilized by autoclave, gamma sterilization, steam sterilization or filter sterilization. Compositions are suitably stored at a range of 4° C. to room temperature (25° C.).

The pharmaceutical composition may comprise, consist or consist essentially of the HAMC gel polymer matrix, one or more local anesthetic agents and water and biocompatible buffers and/or salts, which may include disodium hydrogen phosphate, sodium chloride, potassium chloride and/or potassium dihydrogen phosphate. For example, the constituents may be an HAMC gel polymer matrix in an amount as taught herein, 0.5 to 1.5 wt % of an acid addition salt of the local anesthetic and 10 to 40 wt % of free-base particles of the local anesthetic based on the total weight of the composition; and water and biocompatible buffers and/or salts.

The pharmaceutical compositions described herein are injectable, wherein injection may be, for example, by syringe, via a catheter or other device for delivering a liquid material across the skin such as by microjet (see e.g. U.S. Pat. No. 8,369,942, incorporated by reference herein in its entirety). Alternatively, the composition may be administered by injection by ejecting the material from a syringe without a needle, topically, or into an open wound in some embodiments. When administered via injection, the composition can operate as a depot injection, the composition forming a localized mass. In one embodiment the composition is administered by a single injection. The pharmaceutical compositions as described herein may be administered in a number of ways depending upon the area to be treated. Without limiting the generality of the foregoing, in a particular embodiment, the compositions are administered by subcutaneous, intradermal or intramuscular injection.

In one embodiment, the pharmaceutical composition is administrable with a 10-30 gauge needle, in one embodiment, a 20-25 gauge needle, in one embodiment, without a needle.

The pharmaceutical compositions described herein may be combined with any pharmaceutically acceptable carrier or excipient. As used herein, a "pharmaceutically acceptable carrier" or "excipient" can be a pharmaceutically acceptable solvent, suspending agent or any other pharmacologically inert vehicle selected to facilitate delivery of the pharmaceutical composition to a subject. The excipient may be liquid or solid and is selected, with the planned manner of administration in mind, so as to provide for the desired bulk, consistency, etc., when combined with the other components of the pharmaceutical composition. Examples of pharmaceutically acceptable carriers include one or more of water, saline, phosphate buffered saline, glycerol, ethanol and the like, as well as combinations thereof. Pharmaceutically acceptable carriers may further comprise minor amounts of auxiliary substances such as wetting or emulsifying agents, preservatives or buffers, which enhance the shelf life or effectiveness of the pharmacological agent.

In some embodiments, the pharmaceutically acceptable carrier is phosphate buffered saline or saline.

The pharmaceutical composition as described herein may conveniently be presented in unit dosage form of a single-use syringe that has been sterilized for injection with or without a needle.

In one embodiment, the pharmaceutical composition is 0.4 to 2.4 wt % HA and 1.0 to 3.0 wt % MC with 0 to 26 wt % ropivacaine HCl and 74 to 100 wt % ropivacaine base. The pharmaceutical composition is loaded into a syringe and sterilized using steam. The pharmaceutical composition can vary from 1 mL to 20 mL. The syringe size can also vary from 1 to 20 mL.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

As used herein "subject" refers to an animal being administered a local anesthetic, in one embodiment a mammal, in one embodiment a human patient. As used herein "treatment", and grammatical variations thereof, refers to administering a compound or composition of the present invention, in one embodiment in order to provide localized pain relief. This treatment may be to alleviate pain or the use may be prophylactic to prevent pain. The treatment may require administration of multiple doses, which may be at regular intervals.

In one embodiment, there is provided a method of treating or preventing pain comprising administering, preferably by injection, a therapeutically effective amount of a pharmaceutical composition as described herein.

Without limiting the generality of the foregoing, the present compositions have particular utility in association with surgical anesthesia and the treatment of post-surgical pain. Other uses include the treatment of labor pain; the treatment of chronic pain including but not limited to post-herpetic neuralgia and focal peripheral neuropathies; the treatment of migraine pain; the treatment of rehabilitation pain during physiotherapy; and nerve blocks including but not limited to peripheral nerve block, sciatic nerve block, brachial plexus nerve block, intercostal central neural block and lumbar and caudal epidural blocks.

All documents referenced herein are incorporated by reference, however, it should be appreciated that any patent, publication, or other disclosure material, in whole or in part, that is incorporated by reference herein is incorporated only to the extent that the incorporated material does not conflict with definitions, statements, or other disclosure material set forth in this disclosure. As such, and to the extent necessary, the disclosure as explicitly set forth herein supersedes any conflicting material incorporated herein by reference.

It will be understood that numerous modifications thereto will appear to those skilled in the art. Accordingly, the above description and accompanying drawings should be taken as illustrative of the invention and not in a limiting sense. It will further be understood that it is intended to cover any variations, uses, or adaptations of the invention following, in general, the principles of the invention and including such departures from the present disclosure as come within known or customary practice within the art to which the invention pertains and as may be applied to the essential features herein before set forth, and as follows in the scope of the appended claims.

The embodiments of the invention described above are intended to be exemplary only. The scope of the invention is therefore intended to be limited solely by the scope of the appended claims.

Example 1—Preparation and Sterilization of HAMC Gels

Preparation of HAMC Gel 1.4:3 w/w HAMC with 13.3 mg/mL Ropivacaine (Base form) was prepared as per Table 1 (per mL of gel made).

TABLE 1

| | |
|---|---|
| 14 mg | Sodium Hyaluronate |
| 30 mg | Methylcellulose |
| 13.3 mg | Ropivacaine (Base form) |
| 942.7 µL | Phosphate Buffered Saline |

HAMC hydrogels were prepared through the physical blending of HA and MC in phosphate buffered saline (PBS), (speed-mixed at maximum speed for 30 seconds, centrifuged at 5000 RPM for 1 minute) and allowed to dissolve overnight at 4° C. Ropivacaine particles were dispersed in HAMC using a speedmixer to ensure a uniform suspension, (speed-mixed at maximum speed for 30 seconds, centrifuged at 5000 RPM for 1 minute). Gels were kept at 4° C. until sterilization.

Sterilization of HAMC Gels

HAMC hydrogels were, sequentially, manually mixed with a needle, speed-mixed at maximum speed for 30 seconds, centrifuged at maximum speed for 1 minute and then placed in a glass vial with a loosened cap. The vial containing the HAMC hydrogel was autoclaved at 121° C. for 20 minutes in a beaker with a small amount of water in the bottom of the beaker.

After autoclaving, the cap on the vial was tightened and the vial containing the HAMC hydrogel was placed on ice. Once cooled, the hydrogel was speed-mixed at maximum speed for 30 seconds, centrifuged at maximum speed for 1 minute and then placed on ice or at 4° C. until use.

Example 2—Effect of HAMC Concentration on Swelling and Degradation

To determine the optimal HAMC composition, the swelling of the analgesic-loaded hydrogel was investigated. To investigate swelling, the HA:MC ratio was varied.

Degradation Study of HAMC

Samples were prepared by first recording the mass of 2 mL plastic microtubes and 100 mg of HAMC hydrogel was aliquoted into each microtube. The samples were speed-mixed at maximum speed for 30 seconds in a horizontal position, followed by 30 seconds in a vertical position. The samples were sequentially centrifuged at maximum speed for 30 seconds and then centrifuged in a flat-bottom centrifuge at maximum speed for 10 seconds before being incubated for 30 minutes at 37° C.

Degradation of the HAMC hydrogels was observed by adding 1 mL of warm (37° C.) PBS to the sample tube and immediately removing the PBS. The surface of the hydrogel was gently dried with a rolled Kim Wipe and the mass of the gel was recorded. 1.8 mL of warm PBS was then added to the tube and it was placed in a 37° C. incubator rotating at 45 RPM. This procedure was repeated for several timepoints.

Swelling Ratio Assay

To determine the swelling ratio of ropivacaine-loaded HAMC, the mass of each respective tube was pre-weighed and then 100 mg of analgesic-loaded HAMC was added. Each sample was allowed to gel at 37° C. for 30 minutes. The mass of HAMC at time zero was recorded after adding and immediately removing 1800 µL of pre-warmed to 37° C. PBS, after which fresh PBS was replaced on top of the hydrogel. At each time point (1 h, 2 h, 4 h, 6 h, 24 h, 48 h, 3 days, 4 days, 5 days, 6 days, 7 days, 9 days, 12 days and 15 days), the PBS was completely removed, the total mass of the tube and HAMC measured, and fresh medium added on top of the gel. The swelling ratio describes the fold change in gel mass.

As shown in FIG. 1, analgesic-loaded HAMC formulations containing a higher weight percentage of HA reached a higher maximum swelling ratio and also collapsed faster: 3:3 HAMC doubled in mass, to a maximum ratio of 2.21±0.01. Both the 1.4:3 and 1.4:6 HAMC formulations were minimally swelling and stable up to two weeks, reaching maximum swelling ratios of 1.32±0.13 and 1.67±0.05, respectively. However, if the weight percentage of MC was decreased to 1.4%, the gel was unstable and fell apart almost immediately, demonstrating a minimum MC concentration was required for formation of a stable gel.

Example 3—Effect of HAMC Concentration on Syringeability/Injectability

Figure 2:
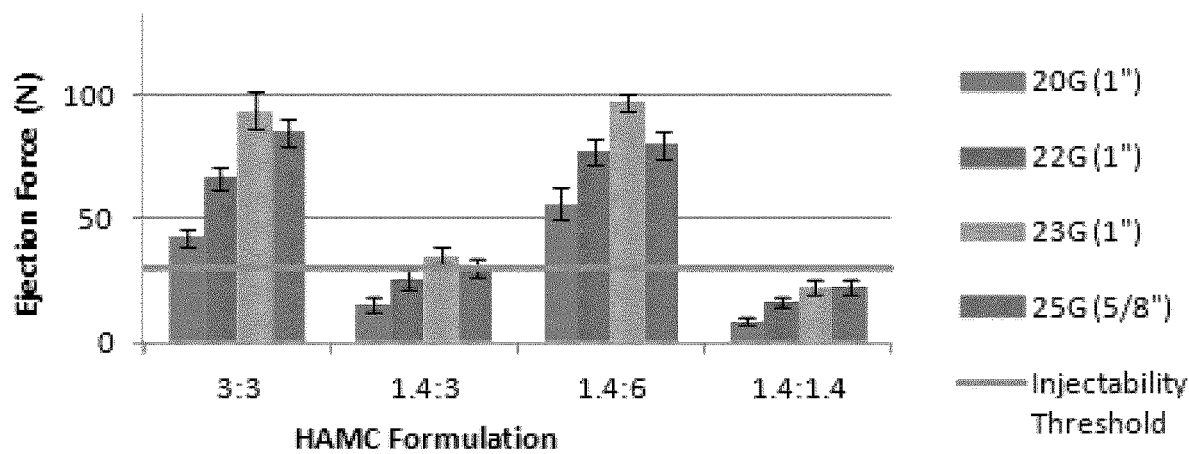
FIG. 2 shows the injectability of different HAMC formulations. The 1.4:3 HAMC was injectable through various needle gauges.

To investigate the injectability of the analgesic-loaded hydrogels, each HAMC formulation was loaded into a 10 mL syringe with a 20, 22, 23, or 25 gauge needle attached. Two concentrations of ropivacaine were tested, 39.9 mg/mL and 75 mg/mL. Using a digital force gauge (M5-50 Force Gauge, Mark-10), the minimum amount of force required to inject each formulation was measured and compared to a manual injectability threshold of 30N. Force was slowly applied to the syringe until gel began to emerge from the tip of the needle. The maximum tension peak force that was applied during the injection process was recorded. This force corresponded to the minimum amount of force required to inject the gel. While the 3:3 and 1.4:6 HAMC formulations were above the manual injectability threshold and were thus not injectable through any of the needle sizes, the 1.4:3 HAMC formulation fell below (or was at) this threshold (FIG. 2). While the 1.4:1.4 HAMC formulation also fell below the threshold for injectability, this gel was not stable.

Example 4—Release Kinetics

Bupivacaine was loaded in HAMC and release profiles were measured in vitro in PBS. Samples for release studies were prepared by first recording the mass of 2 mL plastic microtubes and 100 mg of analgesic-loaded HAMC was aliquoted into each 2 mL microcentrifuge tube. The samples were speed-mixed at maximum speed for 30 seconds in a horizontal position, followed by 30 seconds in a vertical position. The samples were micro-centrifuged at maximum speed for 30 seconds and then centrifuged in a flat-bottom centrifuge at maximum speed for 10 seconds to ensure a planar geometry at the surface. Each sample was then allowed to gel at 37° C. for 30 minutes. At time zero, 1.8 mL of pre-warmed PBS was added to the gel and incubated on an orbital shaker rotating at 45 RPM at 37° C. for 1 h, 2 h, 4 h, 6 h, 24 h, 48 h, 3 days, 4 days, 6 days, and 8 days, after which the PBS was completely removed, collected and replaced with 1.8 mL of fresh, pre-warmed PBS and returned to the orbital shaker rotating at 45 RPM at 37° C. Samples were stored at 4° C. until they were analyzed. Each release sample was analyzed for drug concentration by UV-Vis spectrophotometry at an absorbance wavelength of 210 nm. Following the final time point, the amount of drug remaining in HAMC was extracted by dissolving the HAMC in greater than 1 mL of PBS, by vortexing the tubes for 10 seconds and storing them at 4° C. overnight in a shaker, after which they were vortexed for an additional 10 seconds. The extracted mass was then quantified by UV-Vis spectrophotometry, diluting as necessary if the sample was too concentrated.

As 1.4:3 HAMC was both minimally swelling and easily injectable, per Examples 2 and 3, this formulation was identified as an optimal HAMC concentration and was pursued in further in vitro and in vivo testing.

Figure 3:
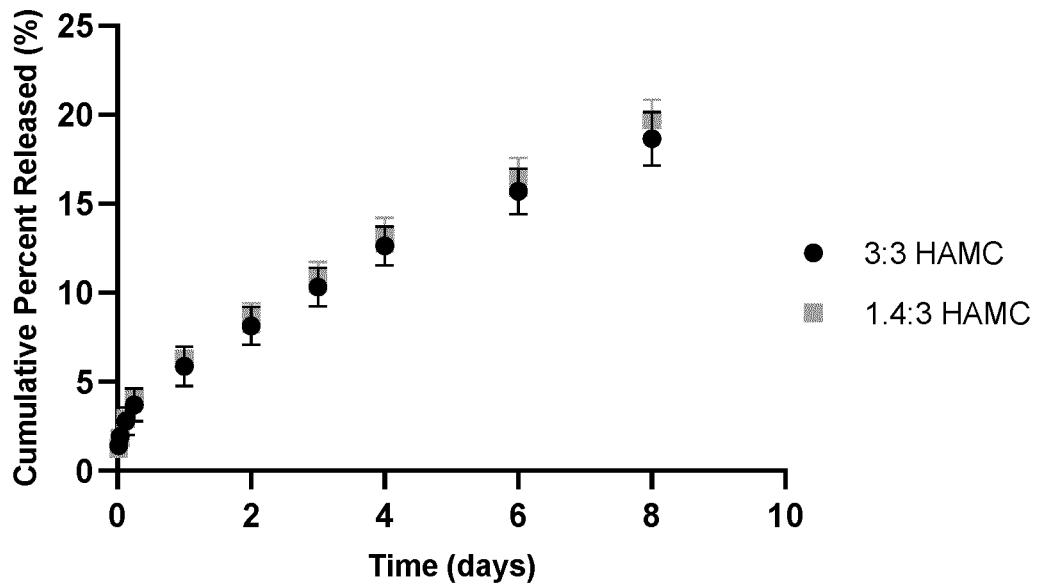
FIG. 3 is a graph showing the effect of varying HA concentration in HAMC on anesthetic release kinetics. Varying the HA concentration had no effect on release kinetics from HAMC.

The concentration of HA was changed, while maintaining the MC concentration, all with 100 mg/mL bupivacaine base, terminally sterilized. Drug release was evaluated in vitro as previously described. An HA concentration of 1.4% (w/v) was sufficient to sustain drug release (FIG. 3).

Figure 4:
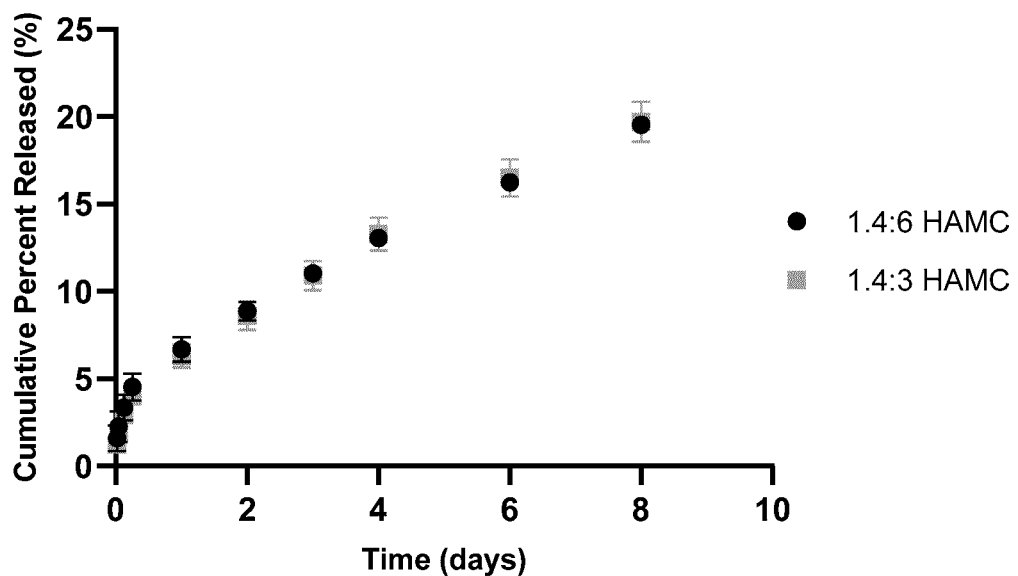
FIG. 4 is a graph showing the effect of varying MC concentration in HAMC on anesthetic release kinetics. Varying the MC concentration had no effect on release kinetics from HAMC.

Next, the effect of MC on HAMC release kinetics was investigated. The concentration of MC was changed, while maintaining the HA concentration, all with 100 mg/mL bupivacaine base, terminally sterilized. Drug release was evaluated in vitro as previously described. An MC concentration of 3.0% (w/v) was sufficient to sustain drug release (FIG. 4).

Example 5—MC Viscosity

Figure 5:
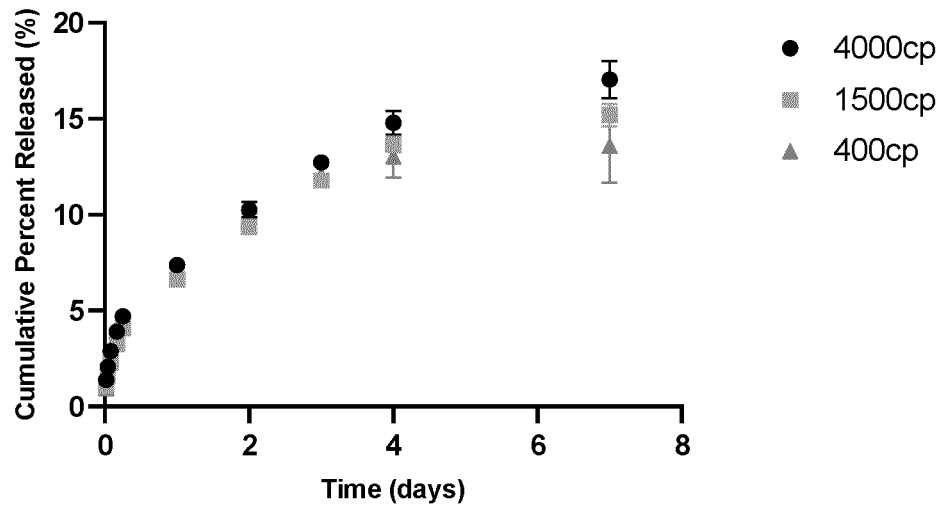
FIG. 5 is a graph showing the effect of varying MC viscosity in HAMC on anesthetic release kinetics. Varying the MC viscosity had no effect on release kinetics from HAMC.

Published literature has demonstrated that the viscosity of MC can change the rate of drug release. HAMC was formulated with MC of different viscosities and the rate of drug release was evaluated. 1.4:3 HAMC using either 4000 cP, 1500 cP, or 400 cP MC with 13.3 mg/mL bupivacaine base was terminally sterilized and tested. Drug release was evaluated in vitro as previously described, with timepoints of 1 h, 2 h, 4 h, 6 h, 24 h, 48 h, 3 days, 4 days, 6 days, 8 days and 14 days. The viscosity of MC did not affect the rate of drug release (FIG. 5).

Example 6—Optimization of Drug Concentration

Figure 6:
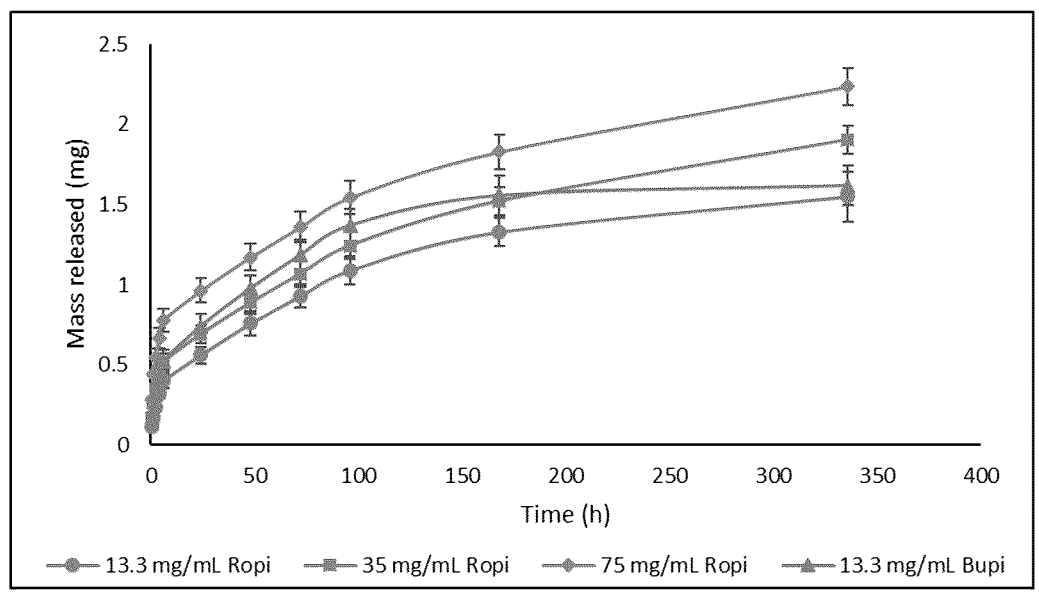
FIG. 6 is a graph showing the effect of varying drug concentration on release kinetics from HAMC. Varying the concentration of ropivacaine had minimal effect on release kinetics from HAMC.

As the dose is scaled-up to a formulation that can be used in humans, the HAMC volume and drug amount will not scale proportionally. Different concentrations of drug in HAMC were tested to evaluate whether scaling to a human dose would pose problems. 1.4:3 HAMC with varying concentrations of ropivacaine base (150 μm particle size) were tested. 13.3 mg/mL, 35 mg/mL, 75 mg/mL ropivacaine base were compared to 13.3 mg/mL bupivacaine base. In vitro release was evaluated as previously described, with timepoints of 1 h, 2 h, 4 h, 6 h, 24 h, 48 h, 3 days, 4 days, 6 days, 8 days 14 days and 28 days. All formulations were terminally sterilized (FIG. 6).

Example 7—Acid:Base Ratio

Figure 7:
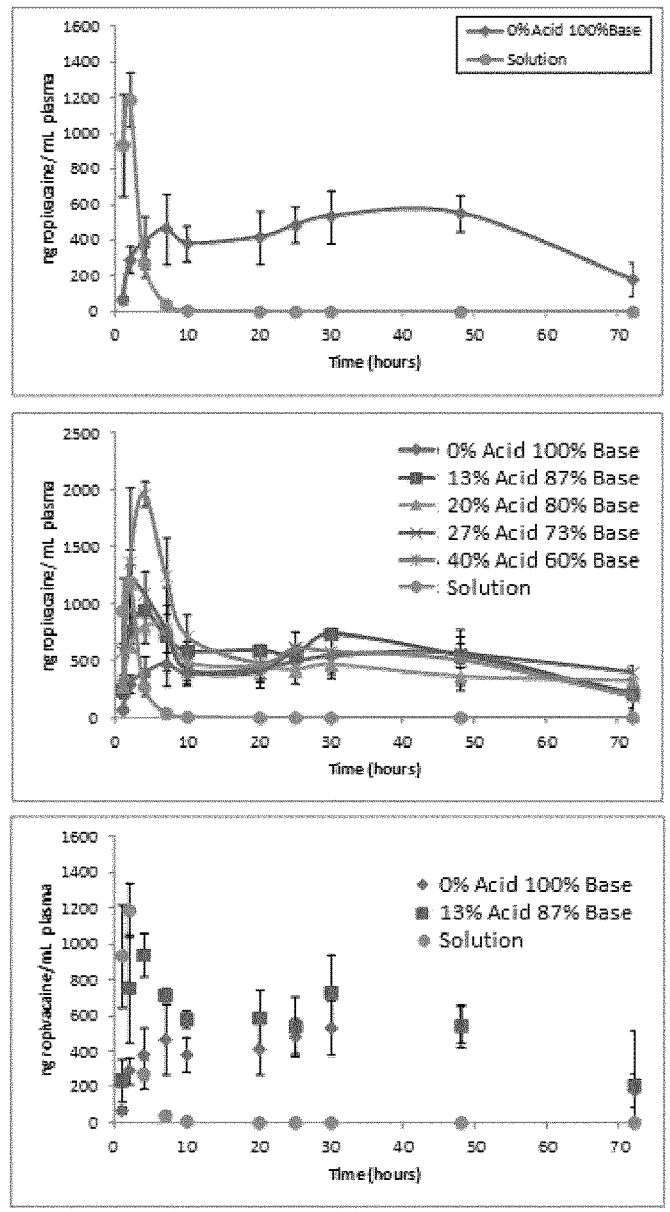
FIG. 7 shows the effect of acid:base ratio of the drug on release kinetics of HAMC in vivo. The table shows values for plasma concentrations at specific time points. Solution is ropivacaine HCl solution. While HAMC combined with ropivacaine base provided a sustained release, the initial rate of release was low. By varying the amount of ropivacaine HCl, the initial rate of release was controlled. Increasing the percentage of ropivacaine HCl in the formulation increased the initial release rate.

The ideal release profile will have a rapid release so that the time of onset is short and a sustained release to provide the required duration of efficacy. In the case of treating post-surgical pain, this is needed so that the patient does not experience pain. To obtain this, it is possible to use different ratios of the acidic and basic forms of the drug. The acidic from of ropivacaine is more soluble that the basic form. Formulations having a greater percentage of the acidic form will have a greater initial release. Formulations were prepared using different ratios of ropivacaine acid:base, injected subcutaneously into rats and the pharmacokinetics evaluated. The inclusion of 13% ropivacaine acid increased the burst release and thereby decreased the time of onset (FIG. 7).

Example 8—Bupivacaine and Ropivacaine Pharmacokinetics

Sciatic Nerve Blockade Model

Male Sprague-Dawley rats, approximately 400-500 g in weight, were anesthetized with 3-5% isoflurane and maintained as required. The left hind leg was shaved, cleaned twice with iodine and 70% ethanol, and a sterile drape placed over the animal to create a sterile field. An incision was made in the skin and the sciatic nerve exposed using a blunt dissection. The treatment was applied, the muscle and incision closed with sutures, and animals allowed to recover under a heat lamp. Controls were injected with vehicle only (i.e. HAMC) or ropivacaine in solution.

Blood samples were taken from the tail veins and quantified using mass-spectrometry. All extractions and mass-spectrometry was carried out by the Analytical Facility for Bioactive Molecules (The Hospital for Sick Children, Toronto, Canada).

To gain insight into the pharmacokinetics of ropivacaine released from HAMC, the sciatic nerve block procedure was performed as described. Animals were treated with ropivacaine-loaded 1.4:3 HAMC at doses of 30, 60, 90 or 120 mg/kg of particulate ropivacaine (<100 μm). Control animals received HAMC alone or ropivacaine in solution at 24 mg/kg. Each animal received approximately 400 μL of treatment. For the HAMC groups, blood was sampled by tail vein puncture at 2 h, 4 h, 6 h, 12 h, 20 h, 30 h, 48 h and 72 h. For the solution groups, blood was sampled by tail vein puncture at 15 minutes, 30 minutes, 1 h, 2 h, 6 h and 24 h. Analysis of plasma samples by liquid chromatography with tandem mass spectrometry (LC-MS/MS) was performed by the Analytical Facility for Bioactive Molecules.

Sensory Block Evaluation

To evaluate the effect of ropivacaine-loaded HAMC in vivo, a ropivacaine dose response study was conducted in the rat model of sciatic nerve blockade with ropivacaine-loaded HAMC as described for the pharmacokinetic study. The pain response was monitored at 2 h, 4 h, 6 h, 12 h, 20 h, 30 h, 48 h and 72 h post-operation by the von Frey and Hargreaves assays. These animals were a separate cohort from those used in the pharmacokinetic studies to avoid any confounding behavioural effects due to tail vein withdrawal.

Von Frey Assay

For the von Frey assay, the 50% withdrawal threshold for mechanical allodynia was measured, as previously described [Shamji, M. F., et al., *Gait abnormalities and inflammatory cytokines in an autologous nucleus pulposus model of radiculopathy*. Spine (Phila Pa 1976), 2009. 34(7): p. 648-54; Pitcher, G. M., Ritchie, J., and Henry. J. L., *Paw withdrawal threshold in the von Frey hair test is influenced by the surface on which the rat stands*. J Neurosci Methods, 1999. 87(2): p. 185-93]. Briefly, animals were placed in individual enclosures on top of a wire mesh and allowed to acclimatize for 20 minutes. Von Frey filaments of increasing stiffness (6, 8, 10, 15, 26, 60, 100, 180, 300 g) were applied sequentially to the mid-plantar region of the hind paw for 3 seconds per measurement. Each filament was applied for a maximum of 6 applications or until the animal sharply withdrew the tested paw 3 times [Shamji, M. F., et al., *Gait abnormalities and inflammatory cytokines in an autologous nucleus pulposus model of radiculopathy*. Spine (Phila Pa 1976), 2009. 34(7): p. 648-54; Pitcher, G. M., Ritchie J., and Henry, J. L., *Paw withdrawal threshold in the von Frey hair test is influenced by the surface on which the rat stands*. J Neurosci Methods, 1999. 87(2): p. 185-93]. If 50% withdrawal was not observed, the next strongest filament was used. If the 50% withdrawal threshold was not observed upon application of the 300 g filament, a value of 300 g (or total block) was recorded. The response from the right uninjured paw was used as an internal control.

Hargreaves Assay

Thermalgesia withdrawal latencies were measured using the Hargreaves assay, as previously described [Wang, Y., et al., *Hydrogel delivery of erythropoietin to the brain for endogenous stem cell stimulation after stroke injury*. Biomaterials, 2012. 33(9): p. 2681-92; Sun, Y. G. and Chen, Z. F., *A gastrin-releasing peptide receptor mediates the itch sensation in the spinal cord*. Nature, 2007. 448(7154): p. 700-3]. In brief, animals were acclimatized in individual enclosures on top of a heated glass plate. The temperature of the glass plate was kept constant for the duration of the experiment by digitally controlled, built-in heating elements. The mid-plantar surface of the hind paw was exposed to a focused radiant heat source and the time for the animal to sharply withdraw its paw was recorded. Three trials per hind paw were recorded, with an interval of at least 2 min separating the trials. A cut-off withdrawal latency of 20 s was used to avoid causing any tissue damage. The response from the right uninjured paw was used as an internal control.

Statistical Analysis

All statistical analyses were performed using GraphPad Prism (GraphPad Software 6, San Diego, CA, USA). Differences among 4 groups were assessed by one-way ANOVA followed by either Dunnett's or Tukey's multiple comparisons test to identify statistical significance. A linear regression was fit to the linear portion (6 hours to 7 days) of each in vitro release profile; the slopes of each line were statistically compared and the lines were extended to theoretically predict time of completed release. The area under the curve (AUC) was calculated for each HAMC-ropivacaine pharmacokinetic profile, and the subsequent AUC vs HAMC-ropivacaine relationship was fit to a linear regression.

Pharmacokinetic Profile of Ropivacaine Improves when Released from HAMC.

A pharmacokinetics study was performed to evaluate the systemic plasma distribution of ropivacaine when delivered either from HAMC or as bolus liquid solution. Four different doses of ropivacaine-loaded HAMC (30, 60, 90 and 120 mg/kg) or a ropivacaine·HCl solution control (24 mg/kg) were delivered to the left sciatic nerve of male Sprague Dawley rats. Ropivacaine·HCl solution has previously been administered to the sciatic nerve of rats at doses as low as 1 mg/kg and up to 50 mg/kg, and the dose was chosen because it fell in the middle of this range. Blood was sampled by tail vein puncture over time, and the amount of ropivacaine was quantified by LC-MS/MS.

Figure 8:
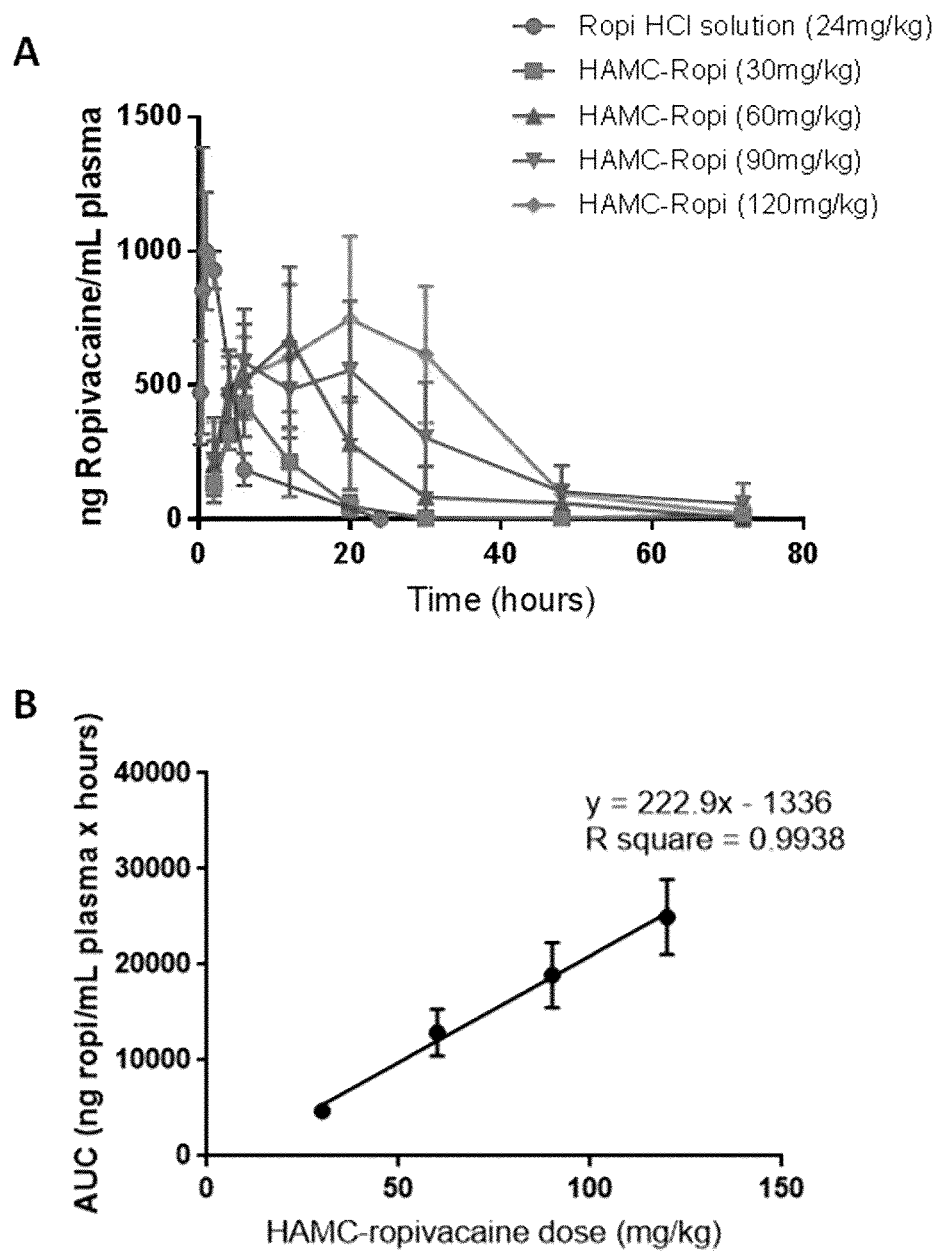
FIG. 8A shows the plasma concentration of ropivacaine following administration of ropivacaine solution (24 mg/kg) or HAMC-ropivacaine (30, 60, 90, 120 mg/kg). By increasing the dose of ropivacaine in HAMC-ropivacaine, the area under the curve (AUC) was increased, while the $C_{max}$ was maintained below that of the ropivacaine solution.
FIG. 8B shows that HAMC-ropivacaine exhibits linear pharmacokinetics. AUC is a function of HAMC-ropivacaine dose.

The pharmacokinetic profiles showed lower maximum plasma concentrations ($C_{max}$), longer time to achieve $C_{max}$ ($T_{max}$) and greater AUC for ropivacaine delivered from HAMC vs. bolus injection of ropivacaine solution (FIG. 8A). For ropivacaine solution, the $C_{max}$ was detected in the plasma at 1 h after injection, at 999.7 ng/mL, before rapidly dropping at 6 h and reaching negligible plasma levels by 24 h. In contrast, when ropivacaine was delivered from HAMC, the resulting pharmacokinetic profiles were extended, with plasma levels of the drug steadily rising before gradually decreasing. Interestingly, although each HAMC-ropivacaine dose was greater than the ropivacaine solution control, the $C_{max}$ of each HAMC-ropivacaine group was lower: the $C_{max}$ of the 30 mg/kg (432.4 ng/mL) and 90 mg/kg (585.8 ng/mL) groups, being significantly lower than that of the ropivacaine solution control. The $T_{max}$ of all HAMC-ropivacaine samples were greater than the ropivacaine solution control, reaching their respective $C_{max}$ at 6 h for the 30 mg/kg dose, 12 h for the 60 mg/kg dose, 6-20 h for the 90 mg/kg dose, and 20 h for the 120 mg/kg dose.

When the AUC was calculated for each of the ropivacaine-loaded HAMC groups and plotted against dose, a linear relationship was observed, with a best-fit line of y=222.9x−1336 with R2=0.9938 (FIG. 8B). Thus the ropivacaine-loaded HAMC system exhibited linear pharmacokinetics and dose proportionality, suggesting that drug clearance was constant over the doses tested.

Nerve Sensory Block of Ropivacaine Extended when Released from HAMC.

Figure 9:
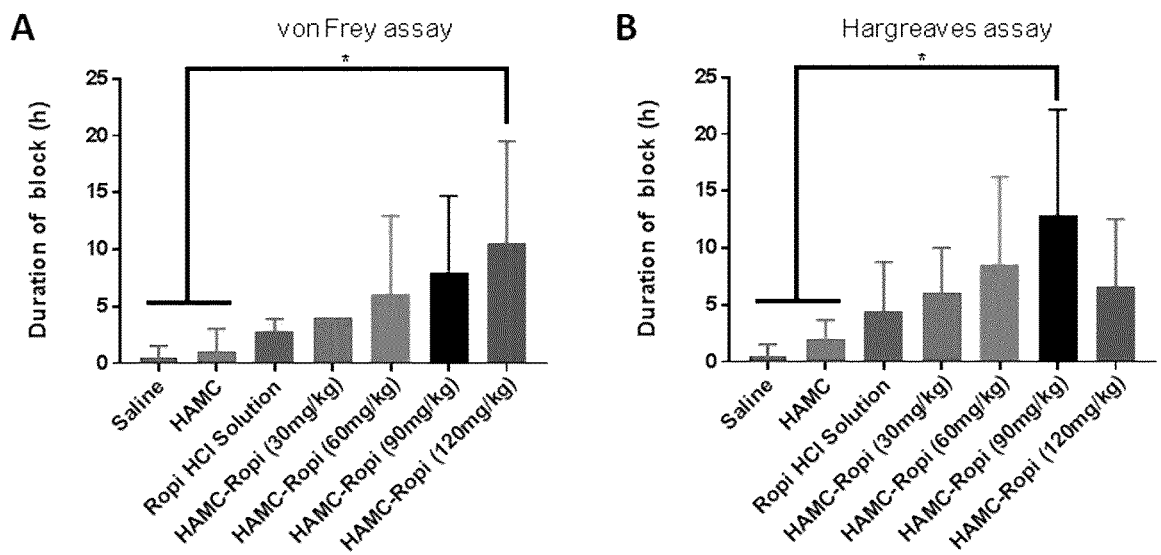
FIG. 9A is a von Frey assay showing that ropivacaine released from HAMC increases the length of sensory block. By increasing the dose of ropivacaine in HAMC-ropivacaine, the duration of efficacy was increased.
FIG. 9B is a Hargreaves assay showing that ropivacaine released from HAMC increases the length of sensory block. By increasing the dose of ropivacaine in HAMC-ropivacaine, the duration of efficacy was increased.

The functional pain response was evaluated by both the von Frey and Hargreaves assays, which are measures of mechanical stimulation and thermalgesia, respectively. The baseline 50% withdrawal threshold for mechanical stimulation was established for each animal prior to surgery. For all treatment groups, the duration in hours for the animal to regain sensation and return to baseline values was reported (FIG. 9A). Higher doses of HAMC-ropivacaine trended toward longer analgesic blocks, as expected in a dose response study. The HAMC-ropivacaine (120 mg/kg) treatment group had a significantly longer block compared to the saline and HAMC alone controls. The second sensory test investigated was the Hargreaves test for thermalgesia. Similar to the von Frey assay, baseline withdrawal latencies were attained prior to the surgery, and the duration for animals to regain sensation and return to baseline levels was measured (FIG. 9B). The HAMC-ropivacaine (90 mg/kg) group had a significantly longer block compared to the saline and HAMC alone controls.

Example 9—Degradation of Sustained Release Compositions In Vitro

Figure 10:
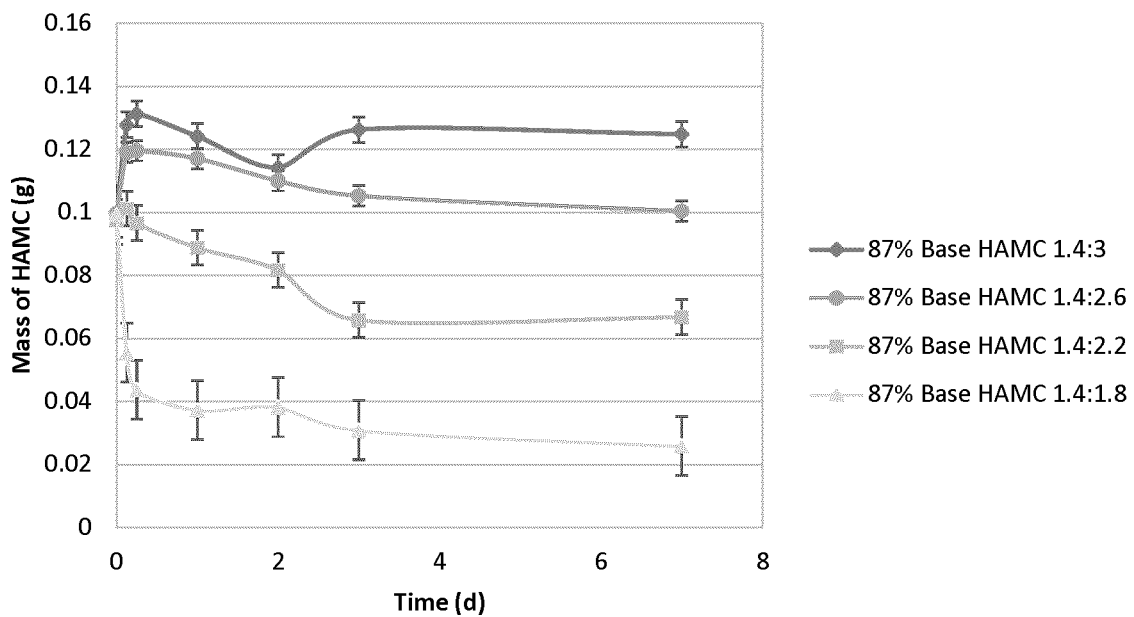
FIG. 10 is a graph showing the effect of lowering the MC concentration on the rate of degradation. By decreasing the concentration of MC, the rate of degradation was increased.
Figure 11:
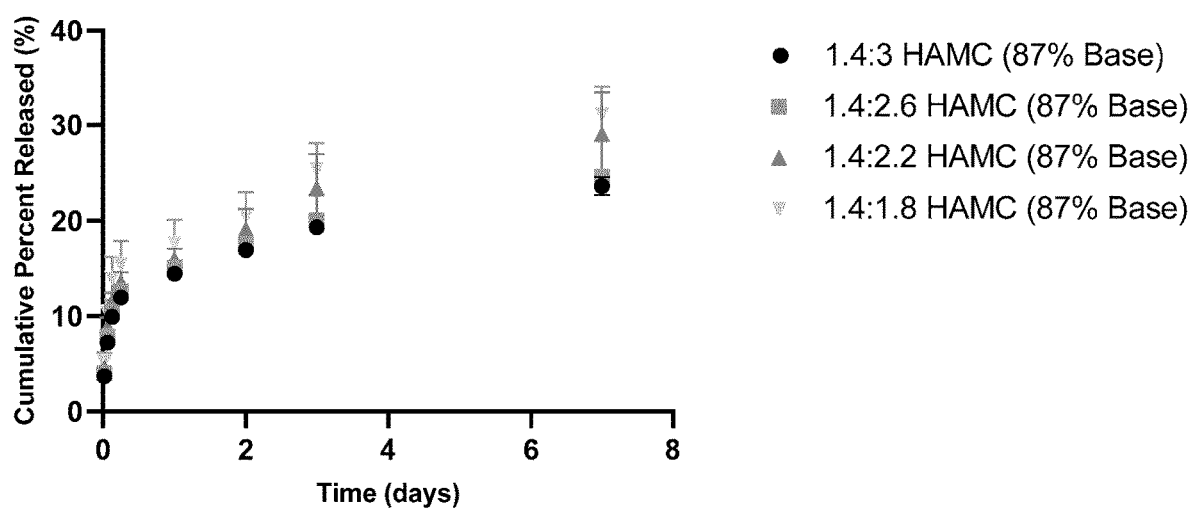
FIG. 11 is a graph showing the effect of MC concentration on in vitro release of ropivacaine in HAMC. While decreasing the MC concentration in HAMC increased the rate of degradation (FIG. 10), minimal effect on the release kinetics of HAMC was observed.
Figure 12A:
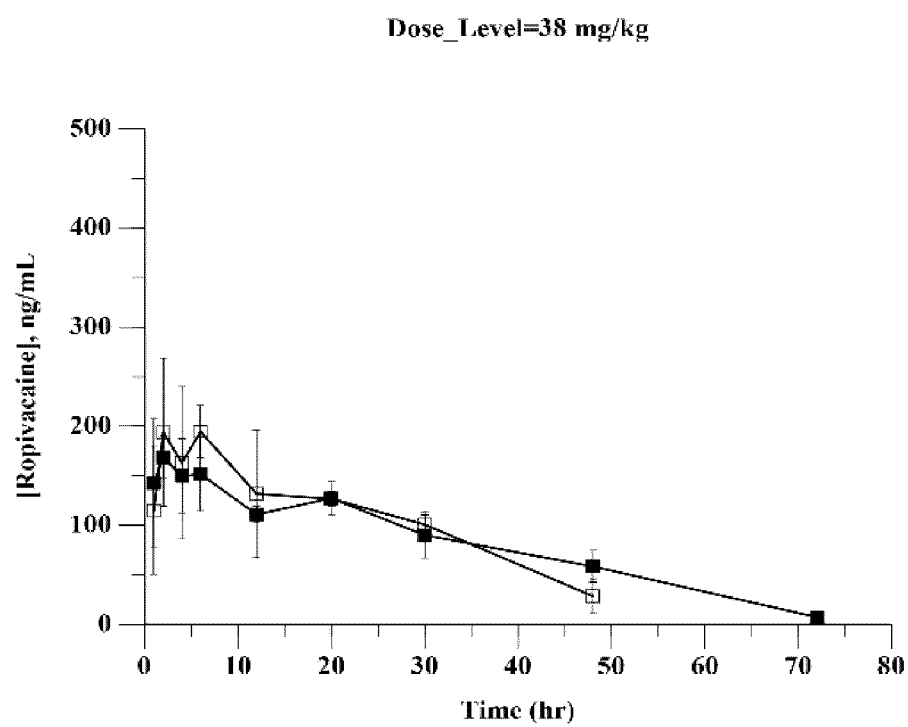
FIGS. 12A-12D is a series of graphs depicting the pharmacokinetic (PK) performance of HAMC low strength HAMC ropivacaine formulation at 38 mg/kg (FIG. 12A), HAMC high strength HAMC ropivacaine formulation at 76 mg/kg (FIG. 12B), HAMC high strength HAMC ropivacaine formulation at 152 mg/kg (FIG. 12C), and 1% Naropin® at 30 mg/kg (FIG. 12D) as described in Example 11 (female rats □, male rats ■).
Figure 12B:
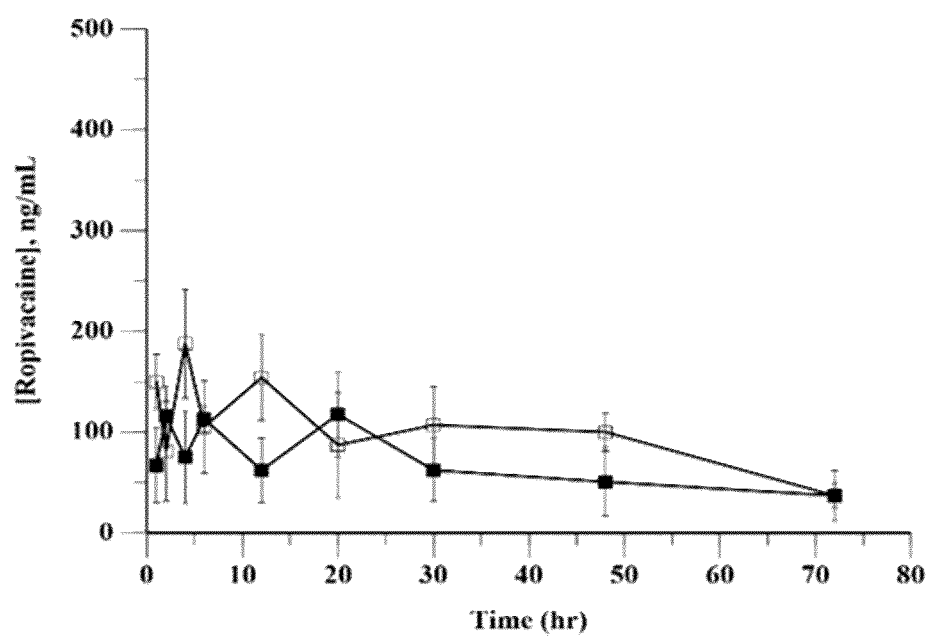
Figure 12C:
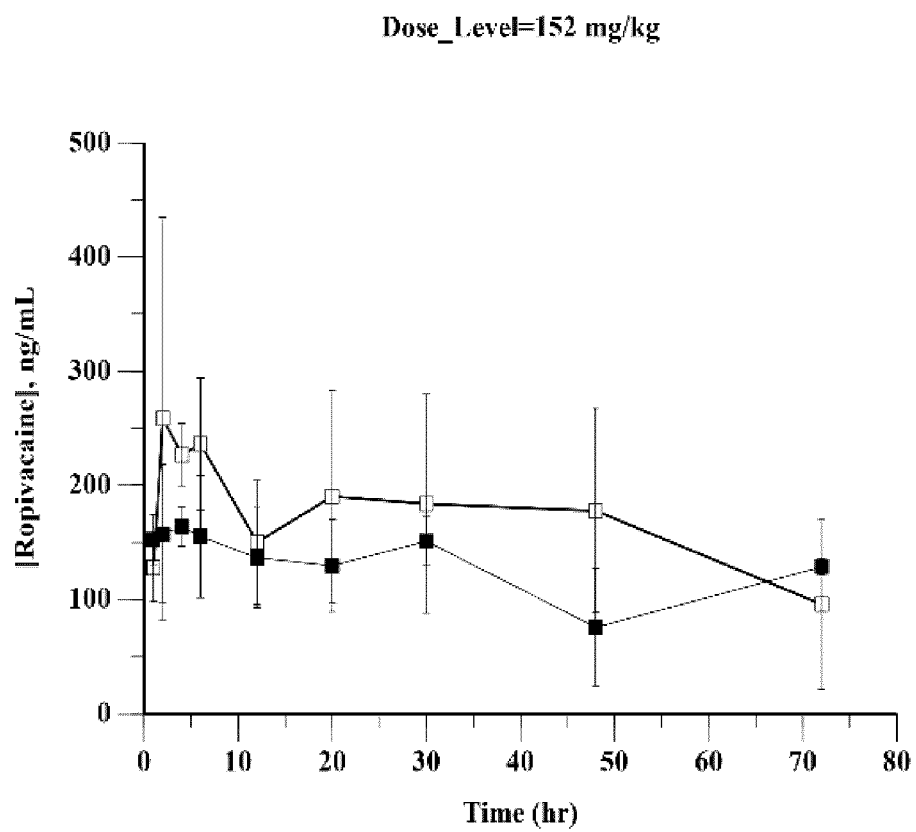
Figure 12D:
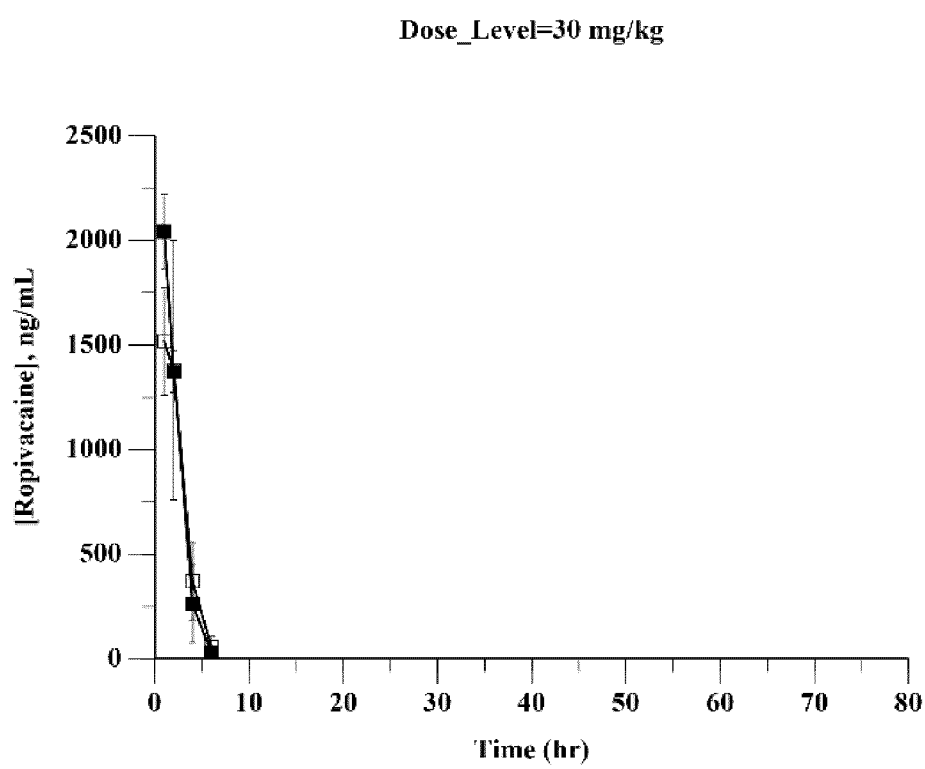

The in vivo resorption of sustained release compositions are important considerations. To accelerate the resorption rate of HAMC, various formulations were prepared where the concentration of HA was held constant at 1.4% (w/v) and the MC concentration decreased (3%, 2.6%, 2.2%, 1.8% (w/v)). Degradation and swelling assays were carried out as previously described. As the concentration of MC was decreased, the rate of degradation increased. Formulations with a concentration of less than 2.6% (w/v) MC with 1.4% HA degraded within one week while providing sustained drug release (FIG. 10, FIG. 11).

Example 10—High Strength and Low Strength Ropivacaine Formulations

Formulations composed of 1.4% HA (14 mg/mL) and 2.0% MC (20 mg/mL) were prepared in two ropivacaine concentrations and include a mixture of immediate release solution of ropivacaine acid addition salt and sustained release ropivacaine free-base particles.

The formulations were prepared through the physical blending of HA and MC in saline. Ropivacaine free-base particles were sieved or milled to form a mixture of particles having a diameter of less than about 200 μm. The ropivacaine particles were dispersed in HAMC hydrogel. Gels were kept at 4° C. until sterilization.

The final formulation was composed of 1.4% HA (14 mg/mL) and 2.0% MC (20 mg/mL), provided in two different concentrations based on ropivacaine HCl equivalence: (i) a low strength formulation (ca. 180-200 mg/mL formulation) containing ca.5-15 mg/mL of a solution of an acid addition salt of ropivacaine and 165-195 mg/mL ropivacaine free-base particles (in ropivacaine HCl equivalent); and (ii) a high strength formulation (ca. 360-400 mg/mL formulation) containing ca. 5-15 mg/mL of a solution of an acid addition salt of ropivacaine and ca. 355-395 mg/mL of ropivacaine free-base particles (in ropivacaine HCl equivalent).

Example 11—PK Performance of the HAMC Ropivacaine Formulations

The PK of HAMC ropivacaine formulations of Example 10 were evaluated relative to 30 mg/kg 1% Naropin® in Sprague-Dawley rats. Each treatment was administered to 6 males and 6 females via the SC route.

Blood samples were collected 1, 2, 4, 6, 12, 20, 30, 48, 72, and 168 hours post-injection. The PK profiles are shown in FIGS. 12A-12D and PK parameters are shown in Table 2. Plasma ropivacaine level was below the limit of quantification (BLOQ) in the 1% Naropin® group 12 hours post-injection, while plasma ropivacaine level was still quantifiable in all the HAMC hydrogel groups up to 72 hours post-injection. The mean $C_{max}$ following HAMC ropivacaine formulation administration was over 5-fold lower than the mean $C_{max}$ following 1% Naropin® administration. The mean AUC of sustained-release for the HAMC ropivacaine formulations increased in a dose-dependent manner; all sustained-release HAMC ropivacaine formulations have a higher AUC compared to 1% Naropin®.

TABLE 2

| Treatment | Dose (mg/kg) | Gender | $T_{max}$ (h) | $C_{max}$ (ng/mL) | $AUC_{last}$ (ng/mL * h) | $MRT_{last}$ (h) |
|---|---|---|---|---|---|---|
| Low strength HAMC ropivacaine formulation | 38 | F | 6 | 194.33 | 5238 | 18.2 |
|  |  | M | 2 | 168.63 | 5799 | 24.3 |
| High strength HAMC ropivacaine formulation | 76 | F | 4 | 187.79 | 6966 | 30.2 |
|  |  | M | 20 | 117.48 | 4704 | 29.5 |
|  | 152 | F | 2 | 258.43 | 12136 | 32.5 |
|  |  | M | 4 | 164.05 | 8713 | 33.5 |
| 1% Naropin ® | 30 | F | 1 | 1518.33 | 4385 | 2.0 |
|  |  | M | 1 | 2042.88 | 4652 | 1.8 |

$AUC_{last}$ = area under the curve to the last measurable time point;
$C_{max}$ = maximum plasma concentration;
F = female;
M = male;
$MRT_{last}$ = mean residence time from the time of dosing to the time of last measurable concentration;
$T_{max}$ = time to maximum concentration Compared to Naropin®, the HAMC ropivacaine formulations produced a $C_{max}$ that was decreased over 5-fold, and plasma ropivacaine concentration was maintained over 3 days. Pharmacodynamic studies demonstrated that the HAMC ropivacaine formulations have a prolonged duration of analgesia, longer than that of Naropin®.

Example 12—Dermal Pinprick Study of HAMC Ropivacaine Formulations

A dermal wheal/pinprick model was used to evaluate the pharmacodynamics of the HAMC ropivacaine formulations of Example 10 in male Sprague-Dawley rats. Subcutaneous injections of low and high strength formulations were compared to both saline and Naropin® injections.

A pinprick was carried out to evaluate sensation or loss of sensation, by using an 18 G needle attached to a 26 g Von Frey filament, which ensures that a consistent force is applied at each time point. The needle was pressed against the surface of the skin for 1 second and the response or lack of response was evaluated. A positive response was classed as either vocalization, movement, or contraction of the underlying muscles. The observer was blinded to the treatment groups to avoid any bias.

The HAMC ropivacaine formulations were injected subcutaneously ~1.2 cm away from the dorsomedial line. The volume of the formulation injected spread sufficiently to raise the skin around the site of injection ~1-2 mm and a bump with a diameter of ~0.7-1.0 cm to appear on the surface of the skin. The pinpricks were applied at the edge of the bump. The response was measured 6 times and the number of negative responses to the 6 pinpricks at each time point was determined; a negative response indicated that the animal did not feel the pinprick and that the anesthetic was effective.

As animals perceive pain differently, a baseline reading of sensation was taken 1 day prior to injection and throughout the experiment, where 6 pinpricks were carried out on contralateral sides, the side that did not receive any injection. The rats that did not exhibit consistent positive pain response on the contralateral side were excluded from data analysis. The data are presented as area under the pain response curve and was calculated using the trapezoidal rule; a higher AUC score indicates a greater degree of anesthesia.

The pinprick assay evaluated sensation at, 1, 2, 4, 8, 24, 30, 48, 72, and 144 hours post-treatment. Maximum anesthetic response was observed at 2 hours post-injection for all groups. When compared to the saline control, Naropin® showed an analgesic effect for 1 day but, there was no significant analgesics effect of Naropin® compared to saline controls at 2 or 3 days post-injection. In contrast, formulations A and B showed a significant analgesic effect compared to the saline control for 1, 2, and 3 days post-injection (see Table 3).

TABLE 3

| Treatment | N | AUC (# of Negative Response * h) | | | $T_{max}$(h) |
| | | Day 1 | Day 2 | Day 3 | |
|---|---|---|---|---|---|
| Low strength HAMC ropivacaine formulation | 16 | 57.03 ± 37.02 | 48.19 ± 38.42 | 30.75 ± 30.02 | 2 |
| High strength HAMC ropivacaine formulation | 17 | 64.88 ± 36.60 | 54.35 ± 39.87 | 38.82 ± 37.60 | 2 |
| 1% Naropin ® | 11 | 54.54 ± 23.79 | 18.27 ± 18.76 | 10.91 ± 16.50 | 2 |
| Saline | 11 | 13.68 ± 14.46 | 3.55 ± 7.21 | 4.36 ± 11.09 | 2 |

AUC = area under the curve (data are presented as mean ± standard deviation);
$T_{max}$ = time to maximum concentration The analgesic effects of the HAMC ropivacaine formulations lasted until Day 3, while the analgesic effects of 1% Naropin® lasted for only one day. Data are presented as mean±SD (standard deviation), n=11-17. Non-parametric pairwise Wilcox test was conducted comparing different treatments each day. Multiple comparisons were adjusted using the "Bonferroni" method. Only 1% Naropin® group ceases to be statistically significant compared to saline group since Day 2.

What is claimed is:

1. A pharmaceutical composition comprising: 1.8 wt % to 3 wt % methylcellulose and 0.1 wt % to 3 wt % hyaluronan in the form of a gel polymer matrix, and at least one local anesthetic agent.

2. The pharmaceutical composition of claim 1, wherein the methylcellulose has a molecular weight between 2,000 g/mol and 500,000 g/mol and the hyaluronan has a molecular weight between 100,000 g/mol and 3,000,000 g/mol.

3. The pharmaceutical composition of claim 1 comprising between 1.8 wt % and 2.2 wt % methylcellulose and between 1.0 wt % and 2.0 wt % hyaluronan.

4. The pharmaceutical composition of claim 1, wherein the pharmaceutical composition is injectable.

5. The pharmaceutical composition of claim 2, wherein the methylcellulose has a viscosity at or above 400 cP.

6. The pharmaceutical composition of claim 1 wherein less than 30% of the local anesthetic agent is released from the pharmaceutical composition within 24 hours of administration.

7. The pharmaceutical composition of claim 1 wherein less than 30% of the local anesthetic agent is released from the pharmaceutical composition within 48 hours of administration.

8. The pharmaceutical composition of claim 1 wherein less than 30% of the local anesthetic agent is released from the pharmaceutical composition within 72 hours of administration.

9. The pharmaceutical composition of claim 1, wherein 30% or less of the pharmaceutical composition remains at the site of administration after 7 days.

10. The pharmaceutical composition of claim 1, wherein the at least one local anesthetic agent is an amide local anesthetic.

11. The pharmaceutical composition of claim 10, wherein the local anesthetic agent is lidocaine, bupivacaine, ropivacaine, or a pharmaceutically acceptable salt thereof.

12. The pharmaceutical composition of claim 11, wherein the local anesthetic agent is ropivacaine and/or a pharmaceutically acceptable salt thereof.

13. The pharmaceutical composition of claim 1, wherein the at least one local anesthetic agent is hydrophobic.

14. The pharmaceutical composition of claim 1, wherein the local anesthetic agent has both an acidic and basic form and wherein the $C_{max}$ of the local anesthetic in the pharmaceutical composition is no greater than the $C_{max}$ of a corresponding dose of the local anesthetic in solution form when administered locally via injection.

15. The pharmaceutical composition of claim 1 wherein the local anesthetic agent has both an acidic form and a basic form and wherein the percentage of the local anesthetic agent in the acidic form and basic form is between 0 to 40% acidic form and 60% to 100% basic form, based on the total weight of the local anesthetic.

16. The pharmaceutical composition of claim 15 wherein the percentage of the local anesthetic agent in the acidic form and basic form is between 0.1% to 27% acidic form and 73% to 99.9% basic form, based on the total weight of the local anesthetic.

17. The pharmaceutical composition of claim 1 consisting or consisting essentially of:
   0.4 to 2.4 wt % hyaluronan;
   1.8 to 3.0 wt % methylcellulose;
   0.5 to 1.5 wt % of an acid addition salt of the local anesthetic; and
   10 to 40 wt % of free-base particles of the local anesthetic; with the remainder of the composition being water and biocompatible buffers and/or salts.

18. A dosage form comprising between 1 mL and 100 mL of the pharmaceutical composition of claim 1.

19. The dosage form of claim 18 comprising between 100 mg and 2000 mg of the local anesthetic agent.

20. A method of treating or preventing pain comprising administering a therapeutically effective amount of the pharmaceutical composition of claim 1 to a subject in need thereof.

21. The method of claim 20 wherein the pain is associated with a minimally invasive procedure and the therapeutically effective amount of the pharmaceutical composition is less than or equal to 20 mL.

22. The method of claim 20, wherein the therapeutically effective amount of the pharmaceutical composition is administered for surgical anesthesia or for the treatment of post-surgical pain.

23. The method of claim 20, wherein the therapeutically effective amount of the pharmaceutical composition is administered to a surgical site or the site of an incision.

24. The method of claim 20, wherein the therapeutically effective amount of the pharmaceutical composition is locally administered as a nerve block.

25. The method of claim 20, wherein the subject is in labor.

26. The method of claim 20, wherein the subject is undergoing a biopsy, a bunionectormy, orthopedic surgery or a hernia procedure.

27. The method of claim 20, wherein the pharmaceutical composition is administered for the treatment of post-burn pain or the subject is donating or receiving a skin graft.

28. A drug depot comprising (i) an aqueous carrier, (ii) from 0.50 to 1.50 wt % of an acid addition salt of an anesthetic selected from lidocaine, bupivacaine, and ropivacaine dissolved in the aqueous carrier, and (iii) from 10 to 50 wt % of free-base particles of an anesthetic selected from lidocaine, bupivacaine, and ropivacaine suspended in the aqueous carrier, wherein the aqueous carrier comprises a biocompatible aqueous gel comprising between 1.8 wt % and 2.2 wt % methylcellulose and between 1.0 wt % and 2.0 wt % hyaluronan.

* * * * *